United States Patent [19]

Houghton et al.

[11] Patent Number: 5,532,209
[45] Date of Patent: Jul. 2, 1996

[54] PROPANIL DISPERSIBLE GRANULE FORMULATION

[75] Inventors: Richard D. Houghton, Harleysville; Linda L. Graham, Flourtown; David P. Krutsch, Betharyes, all of Pa.

[73] Assignee: Rohm and Haas Company, Philadelphia, Pa.

[21] Appl. No.: 465,066

[22] Filed: Jun. 6, 1995

Related U.S. Application Data

[63] Continuation of Ser. No. 887,422, May 21, 1992, abandoned, which is a continuation of Ser. No. 606,642, Oct. 31, 1990, abandoned.

[51] Int. Cl.$^6$ ............................................. A01N 37/22
[52] U.S. Cl. ................................. 504/339; 71/DIG. 1
[58] Field of Search ..................................... 504/339

[56] References Cited

U.S. PATENT DOCUMENTS

| | | | |
|---|---|---|---|
| 3,617,246 | 11/1971 | Duyfjes | 71/79 |
| 3,920,442 | 11/1975 | Albert et al. | 71/92 |
| 3,954,439 | 5/1976 | Papamichael et al. | 71/93 |
| 4,197,112 | 4/1980 | Albert et al. | 71/93 |
| 4,280,833 | 7/1981 | Beestman et al. | 71/100 |
| 4,411,692 | 10/1983 | LeClair | 71/93 |
| 4,870,065 | 9/1989 | Balogh | 514/119 |
| 4,936,901 | 6/1990 | Surgant, Sr. et al. | 71/92 |

FOREIGN PATENT DOCUMENTS

| | | |
|---|---|---|
| 252896 | 8/1987 | European Pat. Off. . |
| 1433882 | 5/1976 | United Kingdom . |
| 89/00079 | 1/1989 | WIPO . |

Primary Examiner—S. Mark Clardy
Attorney, Agent, or Firm—Thomas D. Rogerson

[57] ABSTRACT

A dispersable granular formulation has been developed which contains at least 60% propanil herbicide. This formulation also provides excellent suspensibility and dispersibility characteristics and resists attrition.

18 Claims, No Drawings

PROPANIL DISPERSIBLE GRANULE FORMULATION

This application is a continuation of application Ser. No. 07/887,422, filed Mar. 21, 1992, now abandoned which was a continuation of application Ser. No. 07/606,642, filed Oct. 31, 1990, now abandoned.

BACKGROUND OF THE INVENTION

This invention relates to novel dispersible granule formulations of the herbicide propanil and processes for their preparation.

Water dispersible granular pesticide formulations are known. These formulations are desirable because they avoid the use of potentially toxic solvents and permit the use of easily-disposable paper containers or water soluble containers. Potential exposure of pesticide applicators and the general public to the pesticide or solvent is thereby reduced.

Typical dispersible granular pesticide formulations are described for example in GB 1,433,882, EP 0,252,896 and U.S. Pat. No. 3,920,442. GB 1,433,882 describes a process for preparing dispersible granules by blending premilled, water-insoluble, active ingredient, dispersing agents, disintegrating agent and wetting agents in an aqueous suspension. The aqueous mix is extruded to form granules which are then dried to yield the final product. U.S. Pat. No. 3,920,442 describes water dispersible pesticide aggregates containing 5 to 95% by weight of pesticide. The aggregates are prepared by contacting the finely divided solid ingredients in a fluidized bed with a fine spray of water or a solution of the binder-dispersant followed by drying.

In attempts at making pesticide granules, it has often been found that granules or agglomerates prepared from the formulated wettable powders of the art using well-known agglomerating techniques and using water as the agglomerating agent, are not easily dispersible in water. On the other hand, agglomerates which are readily water-dispersible are often not sufficiently resistant to attrition and form a fine dust fraction upon handling and shipping. If conventional binders are added to make the granules strong, then they are not dispersible in water. Techniques such as tabletting, extrusion and rolling which involve high-pressure compaction of moistened mixtures containing finely divided pesticides, diluents, binder and dispersant, as described in U.S. Pat. No. 3,617,246, lead to dense pellets, tablets, plates, and rods which are subsequently dried and crushed. These techniques have also been used to form granules containing up to 50% of active pesticide, but the resulting granules are not rapidly or completely water dispersible and are not suitable for use in preparing sprayable suspensions.

Low-melting solids such as propanil present an especially difficult problem in the preparation of a dispersible granule formulation. The low-melting solid, herein defined as melting below 100° C., tends to melt or become sticky during or subsequent to the grinding process which is a necessary step in preparing dispersible granules. EP 0,252,896 describes a possible solution to this problem which requires microencapsulation of low-melting pesticides prior to granulation. However, microencapsulation involves additional processing steps and adds to the cost of the overall formulation.

In the case of the herbicide propanil, it has not heretofore been possible to produce a dispersable granular product which combines the features of a high active ingredient content, good suspensibility and dispersant properties as well as resistance to attrition thereby avoiding the formulation of a dust.

Commercial formulations of propanil dispersible granules are available, but these products have deficiencies in that the active ingredient content is relatively low and/or they fail to provide adequate suspension or dispersibility characteristics or are not resistant to attrition.

SUMMARY OF THE INVENTION

This invention relates to dispersible granule formulations of propanil herbicide and processes for preparing these formulations including pan granulation or extrusion of a pre-wet mixture comprising finely-ground active ingredient, wetting agent, dispersing agent and carrier. The dispersible granules produced by these processes contain more than 60% active ingredient and provide good suspensibility and dispersibility characteristics and resist attrition.

DETAILED DESCRIPTION OF THE INVENTION

Propanil herbicide is N-(3,4-dichlorophenyl)propionamide. Dispersible granular (DG) formulations are designated propanil DG or dry flowable (DF). The percentage active ingredient in the formulation is sometimes indicated, as for example, propanil 80 DG or propanil 60 DG.

A DG herbicide composition designed for dispersion in a liquid carrier should ideally have a high content of active material, should be readily dispersible in the carrier and should then form a dispersion which is as stable as possible, requiring the minimum of subsequent agitation for homogeneity. The liquid carrier will, of course, for convenience normally be water. We have now devised a way to make granules which readily break down when they are stirred into a liquid carrier to give a stable dispersion of the active ingredient.

This invention is a dispersible granule comprising at least 60% propanil, said granule having a suspensibility of at least 70% and dispersibility in fewer than 15 cylinder inversions.

In another aspect, this invention is a dispersible granule comprising at least 60% propanil, said granule having a suspensibility of at least 70% and dispersibility in fewer than 15 cylinder inversions; said granule having less than 0.3% by weight of particles less than 45 microns in diameter after 10 minutes of attrition.

In yet another aspect, this invention is a dispersible granule comprising at least 65% propanil, said granule having a suspensibility of at least 70% and dispersibility in less than 15 cylinder inversions.

A more preferred granule of this invention is a dispersible granule comprising at least 80% propanil, said granule having a suspensibility of at least 80% and dispersibility in less than 15 cylinder inversions.

In addition to the active ingredient, propanil, the mixture to be formed into dispersible granules will contain one or more surfactants and, optionally, flow enhancing agents, dispersants, wetting agents and defoaming agents.

According to this invention, there is provided a composition, in granular form, comprising propanil and one or more surfactants.

By granular form, we mean granules substantially all of which have a mean particle size of at least 1 mm., i.e. a particle size much larger than the mean particle size of a powder, the mean particle size of which is measured in microns.

Preferably, the composition contains at least 60% propanil and, more preferably, at least 80% propanil and the total composition preferably has a suspensibility of at least 70%, more preferably, 80% when measured as a 0.9% to 2.0% weight/volume dispersion in standard hard water.

The suspensibility test was performed according to the procedure of the Collaborative International Pesticides Analytical Council (CIPAC) Handbook, Vol. 1, Ed. G. R. RAW (1970), Method Number MT 15.1. Standard hard water (342 ppm as calcium carbonate) was prepared according to CIPAC method MT 18.1.4., also known as Army Hard Water.

Dispersibility is measured by placing one gram of the dispersible granules in 100 ml of 342 ppm hardness water and slowly inverting the test cylinder until the material is completely dispersed. Preferably, dispersion should be complete in 15 or fewer cylinder inversions.

"Attrition" as used in this application is defined as reduction in particle size which occurs when propanil granules are shaken with steel balls as described in Example 1(c)(3).

The term "surfactant" is used in the broad sense to include materials which may be referred to as emulsifying agents, dispersing agents and wetting agents, and the surfactant component may comprise one or more surfactants selected from the anionic, cationic and nonionic type.

Examples of surfactants of the anionic type include soaps, salts of aliphatic monoesters of sulfuric acid such as sodium lauryl sulfate, salts of sulfonated aromatic compounds, for example sodium dodecylbenzene sulfonate, sodium, calcium or ammonium lignosulfonate or butylnaphthalene sulfonate, and a mixture of the sodium salts of diisopropyl- and triiso-propylnapthalene sulfonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters with ethylene oxide and the lecithins and phosphorylated surfactants such as phosphorylated ethylene oxide/propylene oxide block copolymer and ethyoxylated and phosphorylated styryl substituted phenol.

Preferably the surfactant component will comprise at least one wetting agent such as those selected from alkyl naphthalene sulfonates, alkylaryl polyoxyethylene ammonium sulfonates phosphate esters, sulfosuccinates and nonionics such as tridecyl alcohol ethoxylate; and/or at least one dispersing agent such as those selected from the group of napthalene sulfonates, lignosulfonates, polyacrylates and phosphate esters.

Typically the total surfactant component will comprise from 0.1 to 25% and preferably from 1 to 15% by weight of the dry weight of the composition.

In the context of this specification a dispersing agent is a surfactant agent which facilitates the dispersion of the pesticide particles when the product is added to a liquid, for example water. The dispersing agents used are preferably water-soluble ones. Examples of dispersants preferred for the dispersible granule formulations of this invention include: Tamol 731®, Polyfon®H, Polyfon O, Reax® 88B, Morwet® D-425, Reax 45DA, Polyfon T, Polyfon F, Polyfon H, Lignosol™ XD-65, Reax 45L, Reax 85A, Reax 910, Polyfon OD, PC-825 Polyfon T. Most preferred dispersants are: Reax 85A and Polyfon H.

Examples of surfactants preferred as wetting agents for the dispersible granule formulations of this invention include Morwet® B, Morwet EFW, Sellogen® DFL, Morwet IP, Igepon® AC-78, Igepon T-77, Aerosol OT-B, and Surfactant XN-45S. Most preferred wetting agents are Morwet B and Surfactant XN-45S.

All surfactants act as dispersing agents in some degree, and also in some degree as wetting agents; most surface-active agents are however, more efficient in one capacity than the other. The worker of ordinary skill in the formulation art can select a surfactant most suitable for the purpose in view.

Small particles of a low-melting solid such as propanil often tend to stick together thereby causing flow problems in processing the material. Flow aids such as days or silica particles may be used to minimize these problems. Flow aids preferred for the propanil dispersible granular include HiSil® 233, Wessalon® 50S, Cab-O-Sil® M- 5, Wessalon S, Barden® Clay, and Microcel® E. Most preferred are HiSil 233 and Wessalon 50S. The flow aid content of the dispersible granule may vary from 0 to 10% and preferably from 1 to 8%.

Addition of a silicon containing antifoaming agent is desirable to aid in the processing and use of propanil dispersible granules. Defoaming agents may be used in amounts of 0.1% to 5%; a preferred range is about 0.2% to 1.0%. The preferred defoaming agent is Mazu DF- 1300.

Disintegrants, which are water soluble, organic compounds such as starch or sugar or inorganic salts such as sodium acetate or sodium bicarbonate, are sometimes used in dispersible granule formulations. See GB 1,433,882 for example. We have found that these disintegrants have adverse effects on the propanil dispersible granules of this invention. Formulations containing disintegrants were found to be more dusty and disperse less effectively than the granules of this invention.

Dust is herein defined as particles with diameter less than 45 microns. A solid having less than 0.3% by weight dust is defined as "non-dusty" while a solid with more than 4% dust is defined as "very dusty". Solids with 0.3–4% dust are defined as "dusty".

Dust content and resistance to attrition of the propanil dispersible granules of this invention are minimized by forming the granules by the preferred mode of extrusion.

The most preferred composition of this invention comprises by weight percent: propanil 80%; dispersant, Reax 85A, 9.2%; flow aid, HiSil, 4.0%; wetting agent, surfactant XN-45S, 2.0%; defoaming agent, Mazu DF-1300, 0.5%; and water, less than 1%.

Examples of dispersant, wetting agents, flow aids and defoaming agents useful in this invention are shown in Table I.

TABLE I

|  | Producer | Chemical Type |
|---|---|---|
| Dispersants | | |
| Tamol ® 731 | Rohm and Haas Co. Philadelphia, PA 19105 | Sodium carboxylate polyelectrolyte |
| Polyfon ® H Polyfon F Polyfon T Polyfon O Polyfon OD Reax ® 88B Reax 45DA Reax 45L Reax 85A Reax 910 | Westvaco Chemicals P. O. Box 70848 Charleston Hts., SC 29415-0848 | Aliphatic and aromatic sulfonated lignin |
| Lignosol XD-65 | Reed Lignin, Inc. 81 Holly Hill Lane Greenwich, CT 06830 | Sodium lignosulfonate |
| Wetting agents | | |
| Morwet ® B | DeSoto, Inc. | Sodium n-butyl |

TABLE I-continued

| | Producer | Chemical Type |
|---|---|---|
| | 2001 N. Grove<br>Fort Worth, TX 76113 | naphthalene sulfonate |
| Morwet EFW | | Naphthelene sulfonate |
| Morwet IP | | Sodium diisopropyl napthalene sulfonate |
| Sellogen ® DFL | Diamond Shamrock<br>350 Mt. Kemble Ave.<br>Morristown, NJ 07960 | Alkyl naphthalene sulfonate |
| Igepon ® AC-78 | GAF Corp.<br>140 W. 51st. St. | Sodium cocyl isethionate |
| Igepon T-77 | New York, NY 10020 | Sodium methyl aleoyl taurate |
| Aerosol OT-B | American Cyanamid | Sodium dioctyl sulfo succinate |
| Surfactant XN-45S | Rohm and Haas Co.<br>Philadelphia, PA 19105 | Ammonium alkyl/aryl polyoxyethylene sulfate |
| Flow Aids | | |
| HiSil ® 233 | PPG Industries<br>One Gateway Center<br>Pittsburgh, PA 15222 | Silica |
| Wessalon ® 505 | Degussa Corp.<br>Rt. 46, Hollister Rd.<br>Teterboro, NJ 07608 | Silica |
| Wessalon S | | Silica |
| Cab-O-Sil ® M-5 | Cabot Corp.<br>Boston, MA 02110 | Silica |
| Barden ® Clay | J. M. Huber Corp.<br>Rt. #4<br>Macon, GA 30201 | Clay |
| Microcel ® E | Johns-Mansville<br>P.O. Box 5108<br>Denver, CO 80217 | Silicate |
| Defoaming Agents<br>Mazu DF 1300 | Mazer Chemicals<br>3938 Poreti Drive<br>Gurnee, IL 60031 | Silicone and Silica |

The dispersible granules of this invention are prepared by milling one or more surfactants combined with an amount of propanil sufficient to achieve at least 60% active ingredient in said dispersible granules to a particle size of less than 20 microns preferably less than 15 microns and more preferably less than 10 microns thereby forming a premix; then adding to said premix less than 25% water, optionally adding a wetting agent and mixing until a paste is obtained; granulating said paste; and drying the granules thus produced.

The term "pre-mix" as used herein refers to a mixture of active ingredient, dispersant, flow aid and optionally a defoaming agent; the above ingredients are milled to a partial size of 3 to 15 microns, preferably about 8 to 9 microns to form the pre-mix.

The final composition is prepared by adding water, optionally containing a dissolved wetting agent, to the pre-mix, thus, forming a "paste", blending, agglomerating and drying.

Preferred compositions of pre-mix and final composition are shown below.

| Function | Raw Material | Premix % | Final Composition % |
|---|---|---|---|
| Active ingredient | Propanil | 85.9 | 83.3 |
| Dispersant | Reax 85A | 9.5 | 9.2 |
| Flow aid | HiSil 233 | 4.1 | 4.0 |
| Wetting agent | Surfactant XN-45S | — | 2.0 |
| Defoaming agent | Mazu DF-1300 | 0.5 | 0.5 |
| | Water | — | 1.0 |

Agglomeration or granulation may be accomplished by any operable means such as tabletting, pan agglomeration, or extrusion. Extrusion is the preferred method.

Suspensibility of the granule is proportional to the amount of water added to the premix prior to extrusion. However, addition of too much water will cause sticking of the extrudate as it exits the extruder. The relationship of water content of premix and suspensibility is shown in the table below.

| Parts Water per 100 parts premix | % Suspensibility |
|---|---|
| 8 | 63.1 |
| 14 | 78.4 |
| 18 | 84.6 |

The preferred amount of water to be added to the premix is 18 to 20 parts per 100 parts of premix.

After extrusion the dispersible granules are dried. For storage stability, it is important to reduce the residual water to at least 2% and preferably below 1%. High drying temperatures are injurious to the product. The preferred drying temperature is less than 60° C. and more preferably less than 40° C. Drying may be accomplished by any suitable drying means which supplies inert gas at a controlled temperature. A two stage fluid bed dryer is preferred.

A preferred process for producing the propanil dispersible granules of this invention comprises:

(a) milling a mixture of propanil, dispersant and flow aid to a particle size between 3 and 15 microns;

(b) adding a wetting agent dissolved in 12-20% water (based on the total weight of ingredients) to the milled mixture of step (a) and mixing until a homogeneous, extrudable paste is obtained;

(c) extruding the paste obtained in step (b);

(d) drying the extruded granules at a temperature of less than 60° C. to a moisture content of less than about 2%.

The following examples describe the preparation of the propanil dispersable granules of this invention and are intended only to illustrate the invention and not intended to limit the scope of the invention which is defined by the claims.

EXAMPLE 1

Preparation of Propanil 80 DG a) Preparation of Propanil 80 DG Premix

Technical propanil (97%) was melted by heating at 110° C. for 24 hours. The molten material was then poured into aluminum foil lined trays to a depth of about one inch. After cooling at room temperature for 24 hours, the solid was broken up and milled in a coffee mill. The ground material classified as follows:

| Mesh Size | Weight % |
|---|---|
| Larger than 4 mesh | 14.9 |
| 10 to 4 mesh | 40.5 |
| 10 to 20 mesh | 29.3 |
| 20 to 50 mesh | 8.3 |

The coarse milled propanil was blended with other formulation ingredients in a Marion mixer (Mfg. for Rapid Machinery Co., Marion Mixer, Iowa by Texas Div. Tranter Inc. Old Burk Road, Wichita Falls, Tex.) in the following ratio of ingredients:

|  | Weight % |
|---|---|
| Propanil | 85.9 |
| Reax 85A | 9.5 |
| HiSil 233 | 4.1 |
| Mazu DF-1300 | 0.5 |
| Total | 100 | and mixed for 20 minutes.

The above blend was transferred to a Bantam micropulverizer, Mikropul, 10 Chantaur Road, Summit, N.J. 07901, fitted with a 0.42 inch screen and automatic feed; the grinding chamber was cooled with dry ice. The mean particle size of micropulverized product was 43.8 microns.

The micropulverized product was then air milled in an 8" horizontal (pancake) jet mill, Fluid Energy Processing and Equipment Co., 153 Penn Energy, Hatfield, Pa. 19440. An Accu-Rate feeder, Accurate Feeder, 746 E. Milwauke Street, White Water, Wis. 53190 was fitted with a 2" screw feed nozzle positioned to deliver micropulverized material to the air mill. High pressure nitrogen was used for both feeding and grinding to maintain an oxygen concentration below 10%. The ground material was collected in the air bag.

| Air Mill Operating Conditions | |
|---|---|
| Nitrogen feed pressure | 65 psig |
| Nitrogen grind pressure | 60 psig |
| Accurate-rate setting | 100 |

Under these conditions the milling rate was 8–10 lbs./hour. The mean particle size was 9.1 microns. This product constituted propanil 80 DG premix.

b) Preparation of propanil 80 DG

Propanil premix (98.0 parts by weight), Surfactant XN-45S (60% aqueous solution, 3.33 parts by weight) and water (16.67 parts by weight) were mixed in a Kitchen Aid mixer, Hobart, Kitchen Aid Div. Troy, Ohio for approximately 2–3 minutes.

The mixture was transferred to a KAR 130 extruder, Tsu Tsui Rikagaku Kikai Co., Ltd., Japan, fitted with a 1.0 mm screen. After extrusion, the extrudate was air dried to a moisture content of 1–2% at a temperature of less than 40° C.

C.) Measurement of Physical Properties

1. Suspensibility (variation of CIPAC method in duplicate)

One gram of propanil DG was placed in a glass-stoppered graduated cylinder containing 99 rrd of Army Hard Water at 25°. The cylinder was inverted 30 times over a period of 90 seconds and allowed to stand for 30 minutes. The bottom 10 ml was separated, evaporated and dried for 48 hours at 60° C.; and the resulting residue was used to calculate suspensibility by the following formula.

% suspensibility=[1 - weight of residue]×111

2. Dispersibility (in triplicate)

One gram propanil DG was added to 100 ml of Army Hard Water in a 100 ml glass-stoppered graduated cylinder. The cylinder was inverted until the DG was completely dispered and the number of inversions was recorded.

3. Product Attrition Measurement

Ten ⅜ inch steel balls and 50 g propanil DG were placed in the bottom pan of 8 inch diameter stainless steel sieves. The pan was shaken on a Ro-tap sieve shaker with a hammer tapper for 10 minutes.

The steel balls were removed from the pan and the granules were transferred to the top of the nested sieves in the order of 20, 60, 100, 200, 325 mesh and bottom pan. The nested screens were inserted into the Ro-top and shaken for 15 minutes. The amount of residue on each sieve and bottom pan was determined. The weight percent of each fraction was determined by sieving before and after the attrition test.

4. Residual Moisture loss (in duplicate)

Approximately 5 grams DG was weighed to the nearest 0.01 g in a preweighed pan, and dried 24 hours (±1 hour) at 60° C. at approximately 15 mm Hg pressure.

The percent moisture loss was measured by weighing the residue.

5. Disintegration/Suspensibility (specified in GB 1,433, 882 on pg. 4)

One gram DG was added to 100 ml Army Hard Water in a centrifuge tube and inverted 15 times slowly. The tube was then placed in a 30° C. water bath and readings (ml of sediment) were taken at 2, 5, 30 minutes.

After 30 minutes, suspension poured through a 120 mesh screen. The screen washed with 1 liter water and residue weight noted. Results of the above measurements were as follows:

| % Suspensibility | 88.4 |
|---|---|
|  | 88.8 |
| (average) | (88.6) |
| Dispersibility | 13 |
|  | 14 |
|  | 14 |
| (average) | (14) |
| % Moisture loss | 1.1 |
|  | 1.5 |
| (average) | (1.3) |
| Disintegration/Susp. | |
| 2 min (<trace*) | 0.05 ml |
| 5 min (<0.1 ml*) | 0.1 ml |
| 30 min (<0.3 ml*) | 0.3 ml |
| Screen residue | 0 |

*suggested target.

Results of Attrition Test

An increase of 2.4% particles below 840 um (20 mesh) occurred following the attrition test. This increase was confined to particles within the range of 250 um to 74 um. No increase of percent particles below 44 um occurred. Initial percentage below 44 um was 0.2%. Data for the study are given in the following table.

|  | Part. Cut | Sieve Test (Before) | Attrit. Test (After) | Differ. |
|---|---|---|---|---|
| Through a 325 mesh | <44 um | 0.20 | 0.20 | 0 |
| Retained on 325 mesh | 44/74 | 0.16 | 0.14 | −0.02 |
| Retained on 200 mesh | 74/149 | 0.08 | 0.18 | 0.10 |
| Retained on 100 mesh | 149/250 | 0.02 | 1.21 | 1.19 |
| Retained on 60 mesh | 250/840 | 0.10 | 1.23 | 1.13 |
| Retained on 20 mesh | >840 um | 99.44 | 97.04 | −2.40 |
|  |  | 100.00% | 100.00% |  |

EXAMPLE 2

A number of formulations of propanil DG were prepared with active ingredient content ranging from 60.4% to 90.2%. The procedure for preparing these granular formulations followed the general procedure of Example 1, except that Morwet B, Polyfon H and Barden Clay were substituted for Surfactant XN-45S, Reax 85A and HiSil 233, respectively. No antifoam agent was used. The results are shown in the Table II below.

TABLE II

| Ingredients as WT. % |  |  |  |  |  |  |  |  |
|---|---|---|---|---|---|---|---|---|
| Propanil Tech | 60.4 | 65.4 | 70.4 | 75.4 | 75.4 | 80.2 | 85.2 | 90.2 |
| Morwet B | 2.0 | 2.0 | 2.0 | 2.0 | 2.0 | 2.0 | 2.0 | 2.0 |
| Polyfon H | 10.0 | 10.0 | 10.0 | 10.0 | 21.1 | 16.2 | 11.1 | 6.0 |
| Barden Clay | 26.5 | 21.3 | 16.2 | 11.1 | 0 | 0 | 0 | 0 |
| Total | 100 | 100 | 100 | 100 | 100 | 100 | 100 | 100 |
| Suspensibility (%) | 91.7 | 100 | 100 | 100 | 100 | 92.7 | 64.5 | 14.0 |

EXAMPLE 3

Comparison with Competitive Products

1. Comparison of propanil DG with formulations incorporating disintegrants as described in British Patent 1,433,882.

Propanil 80DG was prepared with 0, 2 and 4 percent of the disintegrants sodium bicarbonate and sodium acetate. Various physical properties were measured using air dried, extruded product. Use of disintegrants, at either level, worsened dispersibility in water although there was some slight improvement in suspensibility with 2 percent sodium bicarbonate or 4 percent sodium acetate after 2 and 5 minutes. Samples containing sodium acetate required additional water in the wetting step to allow proper extrusion.

Procedure

Using Propanil 80 DG premix (milled but not extruded), a control and alternative extruded formulations containing 2 and 4 percent disintegrants were made. These were prepared according to the procedure of Example 1 and all compositions used 2 percent (solids) Surfactant XN-45S in the wetting step at the rate of 18:100 water to premix. The complete compositions were:

| Composition | Propanil DG Control | GB 1,433,882 Disintegrants | | | |
|---|---|---|---|---|---|
|  |  | 1 | 2 | 3 | 4 |
| Propanil Premix | 98.0 | 96.0 | 94.0 | 96.0 | 94.0 |
| Surfactant XNJ-45S (60%) | 3.33 | 3.33 | 3.33 | 3.33 | 3.33 |
| Water | 16.67 | 16.67 | 16.67 | 16.67 | 16.67 |
| Sodium Bicarbonate[1] | — | 2.0 | 4.0 | — | — |
| Sodium Acetate[1] | — | — | — | 2.0 | 4.0 |
|  | 118.00 | 118.00 | 118.00 | 118.00 | 118.00 |
| Additional water added to facilitate extrusion | 0 | 2.5 | 3.4 | 4.0 | 6.0 |

[1]anhydrous powder

The composition of propanil premix in the above table was:

|  | Weight % |
|---|---|
| Propanil | 85.9 |
| HiSil 233 | 4.1 |
| Mazu DF-1300 | 0.51 |
| Reax 85 A | 9.5 |
| Total | 100.0 |

The premix and disintegrants, sodium bicarbonate or sodium acetate were mixed together in a Kitchen Aid mixer for approximately 1 minute. The surfactant/water solution was added while mixing and allowed to knead for 2–3 min. Initial compositions with disintegrants which were formulated with the same concentration of water as the control were too dry for extrusion (extrusion process did not form noodles). Additional water was added as indicated in the above table and kneading continued for an additional 1–2 min. The sample was transferred to the small KAR 130 extruder and extruded through the 1.0mm screen. The extrudate was air dried overnight and various measurements were taken.

Measurements

Suspensibility, dispersibility, residual moisture, and disintegration/suspensibility (as specified in GB 1,433,882, pg. 4) were determined as described in Example 1. Results are shown in Table III.

TABLE III

|  | Propanil DG Control | GB 1,433,882 Disintegrates | | | |
|---|---|---|---|---|---|
|  |  | 1 | 2 | 3 | 4 |
| % Sodium bicarbonate | 0 | 2 | 4 | 0 | 0 |
| % Sodium acetate | 0 | 0 | 0 | 2 | 4 |
| g additional water | 0 | 0 | 0 | 4 | 6 |
| % Suspensibility | 88.4 | 90.2 | 89.7 | 88.0 | 87.6 |
|  | 88.8 | 89.6 | 90.0 | 87.7 | 88.6 |
| (average) | (88.6) | (89.9) | (89.8) | (87.8) | (88.1) |
| Dispersibility (ave.) | 13 | 16 | 17 | 21 | 19 |
|  | 14 | 16 | 17 | 21 | 19 |
|  | 14 | 16 | 18 | 23 | 19 |
| (average) | (14) | (16) | (17) | (22) | (19) |
| % Moisture loss | 1.1 | 1.9 | 2.0 | 2.2 | 3.3 |
|  | 1.5 | 1.9 | 1.9 | 2.2 | 3.6 |

TABLE III-continued

|  | Propanil DG Control | GB 1,433,882 Disintegrates | | | |
|---|---|---|---|---|---|
|  |  | 1 | 2 | 3 | 4 |
| (average) Disintegration/Susp. | (1.3) | (1.9) | (1.9) | (2.2) | (3.4) |
| 2 min (<trace*) | 0.05 ml | trace | 0.15 ml | 0.05 ml | trace |
| 5 min (<0.1 ml*) | 0.1 ml | trace | 0.15 ml | 0.07 ml | trace |
| 30 min (<0.3 ml*) | 0.3 ml | 0.25 ml | 0.3 ml | 0.3 ml | 0.25 ml |
| Screen residue | 0 | 0 | 0 | 0 | 0 |

*suggested target

The products of GB 1,433,882 containing disintegrants were rated dusty while the control granules of this invention were rated non-dusty.

2. Comparison of Propanil 80 DG with commercial products

Cedar Chemical Corp., 5100 Poplar, Memphis, Tenn. 38137 produces a 50% propanil dispersible granule. Terra International, Inc., Terra Centre 600 Fourth Street, Sioux City, Iowa 51101, produces a 60% propanil dispersible granule.

Propanil 80 DG was compared with commercial products from Cedar and Terra. Suspensibility was measured initially and after storage at 40° C. and 54° C. for 1 to 4 weeks. The results are shown in Table IV.

The Cedar product was rated very dusty having approximately 5% by weight of particles less than 45 microns in diameter after attrition. The Terra product was rated dusty. In contrast, two lots of the granules of this invention had 0.184% and 0.239% by weight of particles less than 45 microns in diameter after attrition and were rated non-dusty.

TABLE IV

| | | | % Suspensibility | | | | | |
|---|---|---|---|---|---|---|---|---|
| | | | 1 week | | 2 weeks | | 4 Weeks | |
| Mfg. | % Propanil | Initial | 40° C. | 54° C. | 40° C. | 54° C. | 40° C. | 54° C. |
| Cedar | 50 | 29 | 35.4 | 16.0 | 20.7 | 14.6 | 27.5 | 13.8 |
| Terra | 60 | 41.0 | 21.4 | 16.1 | 27.4 | 7.0 | 14.5 | 6.6 |
| Propanil DG #1 | 80 | 89.0 | 91.0 | 88.5 | 88.9 | 88.8 | 89.0 | 88.3 |
| Propanil DG #2 | 80 | 89.6 | 91.2 | 89.2 | 90.0 | 89.3 | 87.4 | 88.1 |
| Propanil DG #3 | 80 | 91.2 | 91.3 | 88.7 | 90.8 | 87.8 | 90.6 | 86.5 |
| Propanil DG #4 | 80 | 91.7 | 90.3 | 86.0 | 87.9 | 83.3 | 88.2 | 86.0 |

Samples #1–#4 of this invention were prepared by the procedure of Example 1.
Sample #4 used Morwet B instead of Surfactant XN-45S as the wetting agent.

Although the invention has been described in regard to its preferred embodiments, which constitute the best mode presently known to the inventors, it should be understood that various changes and modifications as would be obvious to one having ordinary skill in this art may be made without departing from the scope of the invention which is defined in the claims.

We claim:

1. A propanil dispersible granule prepared by a process comprising the steps of:

a. milling a mixture comprising propanil and one or more surfactants to a mean particle size of less than 20 microns;

b. forming a paste comprising the milled mixture and less than 25% water;

c. extruding the paste to produce granules; and d. drying the granules to a moisture content of less than 2% at a temperature of less than 60° C.;

wherein the dispersible granule:

a. comprises at least 60 percent by weight propanil;

b. has a mean granule size of at least 1 millimeter;

c. has a suspensibility of at least 70 percent;

d. has dispersibility in fewer than 15 cylinder inversions; and e. produces less than 0.3% by weight of particles less than 45 microns in diameter after 10 minutes of attrition.

2. The dispersible granule of claim 1 comprising at least 65 percent propanil.

3. The dispersible granule of claim 1 comprising at least 80 percent propanil and having a suspensibility of at least 80 percent.

4. The dispersible granule of claim 1 further comprising a dispersant.

5. The dispersible granule of claim 1 further comprising a flow aid.

6. The dispersible granule of claim 1 further comprising a wetting agent.

7. The dispersible granule of claim 1 further comprising a defoaming agent.

8. The dispersible granule of claim 1, said granule containing essentially no disintegrant.

9. The dispersible granule of claim 4 wherein said dispersant comprises a sulfonated lignin.

10. The dispersible granule of claim 5 wherein said flow aid comprises a silica compound.

11. The dispersible granule of claim 6 wherein said wetting agent comprises a naphthelene sulfonate or a polyoxyethylene sulfate.

12. The dispersible granule of claim 7 wherein said defoaming agent comprises a silicone or silica compound.

13. The dispersible granule of claim 4 wherein said dispersant is Reax 85A or Polyfon H.

14. The dispersible granule of claim 5 wherein said flow aid is HiSil 233 or Wessalon 50S.

15. The dispersible granule of claim 6 wherein said wetting agent is Morwet B or Surfactant XN-45S.

16. The dispersible granule of claim 7 wherein said defoaming agent is Maza DF-1300.

17. The propanil dispersible granule of claim 1 wherein the mixture comprising propanil and one or more surfactants is milled to a mean particle size of front 3 to 15 microns.

18. The propanil dispersible granule of claim 1 wherein the paste comprising the milled mixture is formed with front 12 to 20 percent by weight water.

* * * * *